United States Patent [19]

Witte et al.

[11] Patent Number: 5,407,951
[45] Date of Patent: Apr. 18, 1995

[54] SULPHONAMIDOCYCLOALKANE COMPOUNDS, PHARMACEUTICAL COMPOSITIONS CONTAINING THEM, AND METHODS OF USE THEREOF

[75] Inventors: Ernst-Christian Witte, Mannheim; Karlheinz Stegmeier, Oppenheim; Liesel Doerge, Lampertheim, all of Germany

[73] Assignee: Boehringer Mannheim GmbH, Mannheim, Germany

[21] Appl. No.: 906,339

[22] Filed: Jun. 30, 1992

Related U.S. Application Data

[62] Division of Ser. No. 401,254, Aug. 31, 1989, Pat. No. 5,140,038.

[30] Foreign Application Priority Data

Aug. 31, 1988 [DE] Germany .................. 38 29 455.9

[51] Int. Cl.$^6$ .................... A61K 31/18; C07C 311/16; C07C 311/17
[52] U.S. Cl. .................... 514/381; 514/459; 514/471; 514/522; 514/524; 514/538; 514/562; 514/575; 549/293; 549/323; 558/413; 560/10; 560/12; 562/427; 562/430; 562/621; 562/622; 564/84; 564/86; 564/90; 564/93
[58] Field of Search ............... 562/427, 430, 621, 622; 560/10, 12; 558/413; 564/84, 86, 90, 93; 549/293, 323; 514/459, 471, 522, 524, 538, 562, 575, 381

[56] References Cited

PUBLICATIONS

King et al, Chemical Abstracts, vol. 52 (1958) 7334h.
Uloth et al, Chemical Abstracts, vol. 64 (1966) 4980c.
Berger et al, Chemical Abstracts, vol. 69 (1968) 2543c.
Okano et al, Chemical Abstracts, vol. 77 (1972) 156v.
Prout et al, Chemical Abstracts, vol. 78 (1973) 146998p.
Armarego et al, Chemical Abstracts, vol. 82(1975) 125345r.
Schultz et al, Chemical Abstracts, vol. 107 (1987) 198718j.
Uloth et al, J. Med. Chem., vol. 9, No. 1 (1966) pp. 88–97.
Okano et al, J. Med. Chem., vol. 15, No. 3(1972) pp. 247–255.

*Primary Examiner*—Richard L. Raymond
*Attorney, Agent, or Firm*—Nikaido, Marmelstein, Murray & Oram

[57] ABSTRACT

The present invention provides sulphonamides of the general formula:

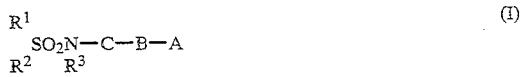

wherein $R^1$ and $R^2$, which can be the same or different, are hydrogen or halogen atoms or $C_1$–$C_6$-alkyl, trifluoro-methyl, cyano, carboxyl, alkoxycarbonyl, aminocarbonyl, N-alkylaminocarbonyl or N,N-dialkylaminocarbonyl radicals or, when $R^1$ and $R^2$ are alkyl radicals ortho to one another, $R^1$ and $R^2$ together with the carbon atoms to which they are attached, form a saturated or unsaturated $C_5$–$C_7$-alkylene ring, $R^3$ is a hydrogen atom, an alkyl radical containing up to 6 carbon atoms, an acyl radical, a phenylalkyl or phenylalkenyl radical, the phenyl moiety of which can be substituted by halogen, alkyl or trifluoromethyl, C is a $-(CH_2)_m$—radical, in which m is 0, 1, 2 or 3, or a branched $C_2$–$C_5$-alkylene radical, whereby a methylene radical —$CH_2$— of the group C can be replaced by an oxygen or sulphur atom or by a hydroxymethylene radical —CHOH—or carbonyl group —CO—, B is a 1,2-, 1,3-, 1,4-cyclohexylidene or 1,2- or 1,3-cyclopentylidene radical.

23 Claims, No Drawings

SULPHONAMIDOCYCLOALKANE COMPOUNDS, PHARMACEUTICAL COMPOSITIONS CONTAINING THEM, AND METHODS OF USE THEREOF

This is a division, of application Ser. No. 07/401,254 filed Aug. 31, 1989, now U.S. Pat. No. 5,140,038.

The present invention is concerned with new sulphonamidoalkyl-cycloalkane compounds, processes for the preparation thereof and pharmaceutical compositions containing them.

The new sulphonamides according to the present invention are compounds of the general formula:

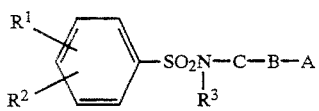

wherein $R^1$ and $R^2$, which can be the same or different, are hydrogen or halogen atoms or $C_1$–$C_6$-alkyl, trifluoromethyl, cyano, carboxyl, alkoxycarbonyl, aminocarbonyl, N-alkylaminocarbonyl or N,N-dialkylaminocarbonyl radicals or, when $R^1$ and $R^2$ are alkyl radicals ortho to one another, $R^1$ and $R^2$, together with the two carbon atoms to which they are attached, form a saturated or unsaturated $C_5$-$C_7$ alkylene ring $R^3$ is a hydrogen atom, an alkyl radical containing up to 6 carbon atoms, an acyl radical, a phenylalkyl or phenylalkenyl radical, the phenyl moiety of which can be substituted by halogen, alkyl or trifluoromethyl, C is a —$(C_2)_m$— radical, in which m is 0, 1, 2 or 3, or a branched $C_2$-$C_5$-akylene radical, whereby a methylene radical —$CH_2$— of group C can be replaced by an oxygen or sulphur atom or by a hydroxymethylene radical —CHOH— or a carbonyl group —CO—, B is a 1,2 -,1,3- or 1,4-cyclohexylidene radical or a 1,2- or 1,3-cyclopentylidene radical, A is a $C_1$-$C_6$-alkyl, hydroxy- $C_1$-$C_6$-alkyl, carboxyl, carboxy- $C_1$-$C_6$-alkyl, carboxy- $C_1$-$C_6$-alkoxy, tetrazolyl, tetrazolyl- $C_1$-$C_6$-alkyl, tetrazolyl-$C_1$-$C_6$-alkoxy, tetrazolylaminocarbonyl-$C_1$-$C_6$-alkoxy $C_1$-$C_6$-alkyl or tetrazolylaminocarbonyl- $C_1$-$C_6$-alkoxy radical or A is a -D-$R^4$ radical, in which D is a —CO— or —CHOH—group and $R^4$ is a hydrogen atom or a $C_1$-$C_5$-alkyl, hydroxy- $C_1$-$C_5$-alkyl, carboxyl, carboxy-$C_1$-$C_5$-alkyl, tetrazolyl or tetrazolyl- $C_1$-$C_5$-alkyl radical and in all cases in which A contains a carboxyl group, this can be replaced by a hydroxamic acid radical —CO—N(OH)$R^5$, in which $R^5$ is a hydrogen atom or a $C_1C_5$- alkyl radical, and when A contains a carboxyl or hydroxyl group optionally also the lactones as well as the pharmacologically acceptable salts, esters and amides and also the optically-active forms and the cis and trans isomers thereof.

From European Patent Specification No. 0,031,954 are known phenylcarboxylic acids which are substituted in the 4-position by sulphoamidoalkyl radicals. Similar compounds in which the carboxylic acid group is replaced by substituted alkyl, alkenyl or alkylcarbonyl radicals are described in European Patent Specification No. 0,221,344. Furthermore, from European Patent Specification No. 0,239,907 are known phenoxyalkylcarboxylic acid derivatives in which the sulphonamidoalkyl radical is in the ortho- or meta-position to the phenoxyalkylcarboxylic acid radical.

Surprisingly, we have now found that compounds with new and valuable pharmacological properties are obtained when, in the compounds known from the above-mentioned prior art, the phenyl group present is replaced by a cyclohexylidene or cyclopentylidene radical.

The new compounds of general formula (I) show an excellent antagonistic action towards thromboxane $A_2$ as well as against prostaglandin endoperoxides and have an activity which is superior to that of the compounds known from the prior art. They inhibit the aggregation of blood platelets and prevent the constriction of the smooth musculature, as well as bronchoconstriction. Furthermore, they are valuable medicaments for the treatment of pathological changes of the kidney function.

These properties make them valuable medicaments for the treatment of, for example, cardiovascular diseases and of asthma and for the prophylaxis of the shock lung. Furthermore, they can be used in the case of or-an transplants and kidney dialysis and are suitable for the prevention of recidivity in the case of stomach ulcers. An especial importance lies in the possibility of favourably influencing or preventing thrombotic processes. They can be used for the treatment of peripheral arterial occlusive diseases and can be used, for example, against cerebral ischaemic states.

If $R^1$, $R^2$, $R^3$ or A are lower alkyl radicals, then there are to be understood thereunder unbranched and branched radicals containing up to 6 carbon atoms, the methyl, butyl and n-hexyl radicals being preferred.

If $R^1$ and $R^2$ together form a ring, then a six-membered ring is preferred. Especially preferred in this sense is the case in which $R^1$ and $R^2$ together with the ring to which they are attached, form an α- or β-napthyl or a tetrahydronaphthyl radical which can possibly be substituted by the groups defined in the case of $R^1$ and especially by halogen atoms.

The halogen atoms are fluorine, chlorine or bromine, chlorine and bromine being preferred.

The tetrazolyl radical is especially the 1H-tetrazol-5-yl radical. As phenylalkyl radicals $R^3$, there can be used those with up to 3 carbon atoms in the alkyl moiety, in which case the phenyl radical is substituted especially by halogen atoms. By phenylalkenyl radicals $R^3$ are to be understood radicals in which the alkenylene moiety contains 3 or 4 carbon atoms. Here, too, the phenyl moiety can possibly be substituted by halogen atoms.

The acyl radicals $R^3$ are derived from aliphatic carboxylic acids containing 2 to 6 carbon atoms and from arylaliphatic, preferredly phenylalkyl and aromatic carboxylic acids. Thus, for example, $R^3$ can be an acetyl, formyl or benzoyl radical.

C preferably has the meaning —$(C_2)m$—, in which m is 0, 1, 2 or 3. B is preferably a cyclohexylidene radical in which the substituents A and C can be in the cis or trans position to one another and the substitution is preferably in the 1,4- or 1,3-position.

A is defined as being an alkyl radical containing up to 6 carbon atoms or as an alkyl radical containing up to 6 carbon atoms which carries a terminal hydroxyl function. Furthermore, A can be a carboxyl group, a tetrazolyl radical or a $C_1$-$C_5$-alkyl radical with a terminal carboxyl or tetrazolyl radical. The just defined alkyl radicals can, in each case, be substituted by a function containing an oxygen atom, i.e. by a hydroxyl or oxo group.

Furthermore, A can preferably be a carboxy-$C_1$-$C_5$-alkoxy or tetrazolyl-$C_1$-$C_5$-alkoxy radical but especially an oxyacetic acid radical or a tetrazolylmethoxy radical.

The groups A set out in the following are preferred:
1. A is an unbranched or branched saturated alkyl radical and especially one of the general formula:

—$(CH_2)_{p-1}CH_3$, wherein p is a number of from 1 to 6.
2. A is an unbranched or branched saturated alkyl radical which carries a terminal carboxyl function or a tetrazolyl radical and especially one of the general formulae —$(CH_2)_{p-1}$—COOH and —$(CH_2)_{p-1}$—tetrazolyl, wherein p is a number of from 1 to 6.
3. A is an unbranched or branched saturated alkyl radical which carries a terminal hydroxyl group and especially one of the general formula:

—$(CH_2)_p$—OH in which p is a number of from 1 to 6.
4. A is a —D—$R^4$ radical, wherein D is a carbonyl group —CO— and
   a) $R^4$ is an unbranched or branched saturated alkyl radical containing up to 5 carbon atoms and especially one of the general formula:

—CO—$(CH_2)_{p-2}$—$CH_3$ wherein p is a number of from 2 to 6;
   b) $R^4$ is an unbranched or branched saturated alkyl radical containing up to 5 carbon atoms which carries a terminal hydroxyl group and especially one of the general formula:

—CO—$(CH_2)_{p-1}$—OH wherein p is a number of from 3 to 6;
   c) $R^4$ is an unbranched or branched alkyl radical with a terminal carboxyl or tetrazolyl radical and especially one of the general formula:

—CO—$(CH2)_{p-2}$—COOH and

—CO—$(CH_2)_{p-2}$—tetrazolyl wherein p is a number of from 3 to 6 but preferably of from 4 to 6.
5. A is a D-$R^4$ radical in which D is a —CHOH— group and $R^4$ has the above-given meaning and especially one of the following general formulae:
   a) —CHOH—$(CH_2)_{p-2}$—$CH_3$, wherein p is a number of from 2 to 6;
   b) —CHOH—$(CH_2)_{p-1}$—OH, wherein p number of from 3 to 6;
   c) —CHOH—$(CH_2)_{p-2}$—COO, wherein p is a number of from 4 to 6;
   d) —CHOH—$(CH_2)_{p-2}$-tetrazolyl, wherein p is a number of from 4 to 6.
6. A is a —O—$(CH_2)_q$—COOH radical, wherein q is a number of from 1 to 5.

Especially preferred are the following meanings of the radicals $R^1$, $R^2$, $R^3$, A, B and C:

$R^1$ or $R^2$ a hydrogen, chlorine or bromine atom or a methyl, n-butyl and n-hexyl, trifluoromethyl, cyano or aminocarbonyl radical. However, preferred for $R^1$ and $R^2$ is a hydrogen atom or the mono-substituted derivatives, preferably in the 4-position of the phenyl ring $R^3$ hydrogen, a methyl, n-butyl or n-hexyl radical; acetyl, n-hexanoyl or benzoyl; benzyl; phenethyl or cinnamyl, the phenyl moieties of which can be substituted by halogen, especially by chloride.

C the group $(CH_2)_m$—wherein m is 2 or 3 or the group —O—$CH_2$—, —$CH_2$—$CH_2$—O—, —$CH_2$—CO— or —$CH_2$—CHOH—.

B 1,4-cyclohexylidene, wherein the substituents are in the cis or trans position.

A an ethyl, butyl or hexyl radical or also a carboxyl or 1H-tetrazol-5-yl radical or an alkyl radical terminally substituted by one of these two groups. In this case, there are especially preferred: A=carboxyl, 1H-tetrazol-5-yl, carboxymethyl, carboxypropyl or carboxybutyl and the 1H-tetrazol-5-yl analogues thereof. Especially preferred groups A as given under point 4a) include, for example, acetyl, butyryl and hexanoyl, of type 4b) hydroxybutanoyl and of type 4c) 3-carboxypropanoyl.

For type 5, as especially preferred radicals A are to be mentioned: for type 5a) the 1-hydroxyethyl, 1-hydroxybutyl and 1-hydroxyhexyl radicals; for type 5b) the 1,4-dihydroxybutyl radical and for type 5c) the 1-hydroxy-3-carboxypropyl) and 1-hydroxy-3-(1H-tetrazol-5-yl)-propyl radical. For type 6, the oxyalkylcarboxylic acid radical ms especially preferably the oxyacetic acid with q=1.

When A is an alkyl radical terminally substituted by a hydroxyl group, there are especially preferred the 2-hydroxyethyl, 4-hydroxybutyl and 6-hydroxyhexyl radicals.

When the group A contains carboxyl groups, the present invention also includes the salts, esters and amides thereof and when A contains not only a carboxyl group but also a hydroxyl group, the "internal esters", i.e. the lactones, are also included.

By the oxyalkylcarboxylic acids are especially preferred the oxyacetic acids and by the tetrazolyl-$C_1$-$C_5$-alkoxy compounds those with a (1H-tetrazol-5-yl)-methoxy radical.

As esters, those are preferred with lower monohydroxy alcohols, for example methanol or ethanol, or with polyhydroxy alcohols, for example glycerol, but there are also included those alcohols which contain other functional groups, for example ethanolamine.

As amides, there are especially preferred the tetrazolyl-5-amides, for example the acetic acid tetrazolylamides, i.e. A=—$CH_2$—CO—NH—tetrazolyl. Amides which are also preferred are the hydroxamic acids, for example cyclohexyloxyacetic acid-N-hydroxylamides, i.e. A=—O—$CH_2$—CONHOH.

If a compound of general formula (I) contains an asymmetric carbon atom, then the present invention includes not only the pure optical isomers but also the mixtures/racemates thereof. If the molecule contains double bonds, then the present invention includes the pure E (entrogen, trans) and Z (zusammen, cis) isomers, as well as mixtures thereof. With regard to the substituents in the cyclohexyl ring, there are included not only the cis but also the trans isomers.

The new compounds of general formula (I) according to the present invention can be prepared by one of the following methods:

a) an amine of the general formula:

$$HN-C-B-A \quad \text{(II)}$$
$$\phantom{HN-}|$$
$$\phantom{HN-}R^3$$

in which $R^3$, A, B and C have the above-given meanings, is reacted in known manner with a sulphonic acid of the general formula:

$$R^1-\text{C}_6\text{H}_3(R^2)-SO_2OH \quad \text{(III)}$$

in which $R^1$ and $R^2$ have the above-given meanings, or with a derivative thereof. Instead of the free amine (II), there can also be used a salt thereof.

b) a sulphonamide of the general formula:

$$R^1-\text{C}_6\text{H}_3(R^2)-SO_2NH-R^3 \quad \text{(IV)}$$

in which $R^1$, $R^2$ and $R^3$ have the above-given meanings, is reacted with a compound of the general formula:

$$X-C-B-A \quad \text{(V)}$$

in which A, B and C have the above-given meanings and X is a reactive group

If A contains a hydroxyl group, in some cases it is advantageous to use a compound (V) which, instead of the hydroxyl group, contains a carboxy group or an ester function or possibly both. Subsequent to the reaction between (IV) and (V), this group is reduced to the hydroxyl function.

c) for the preparation of compounds (I) in which $R^3$ has the above-given meaning but is not a hydrogen atom, there can also be used a subsequent introduction of $R^3$ by reacting a compound of the general formula:

$$R^1-\text{C}_6\text{H}_3(R^2)-SO_2NH-C-B-A \quad \text{(Ia)}$$

in which A, B, C, $R^1$ and $R^2$ have the above-given meanings, with a compound of the general formula:

$$R^3-X \quad \text{(VI)}$$

in which $R^3$ is other than a hydrogen atom.

In the case of the presence of hydroxyl groups in A, that said above under b) applies accordingly.

d) For the introduction of hydroxyl groups into A, there can be used the following processes:
  1. reduction of a carbonyl group
  2. reduction of a carboxylic acid or carboxylic acid ester group
  3. simultaneous reduction of both.

e) For the preparation of compounds (I) in which A is $-O-(CH_2)_q-COOH$, there can also be used the reaction of substituted cycloalkanols of the general formula:

$$Z-N(R^3)-\text{cycloalkyl}(CH_2)_n-OH \quad \text{(VII)}$$

in which Z and $R^3$ have the function of a protective group for the amino group and n is 1 or 2, with a halocarboxylic acid of the general formula:

$$\text{Hal}-(CH_2)_q-COOH \quad \text{(VIII)},$$

and possible subsequent splitting off of the protective group and reaction of the amino group with a sulphonic acid of general formula (III).

f) For the preparation of compounds (I) in which A contains a 1H-tetrazolyl-5-yl radical, the corresponding nitriles are used as starting materials which are cyclised to tetrazoles by reaction with hydrazoic acid.

As reactive derivatives of the sulphonic acids (III), there are especially preferred the halides, as well as the esters. The reaction of the sulphonic acid halides with compounds of general formula (II) advantageously takes place with the addition of an acid-binding agent, for example an alkali metal acetate, sodium hydrogen carbonate, sodium carbonate, sodium phosphate, calcium oxide, calcium carbonate or magnesium carbonate. However, this function can also be undertaken by organic bases, for example pyridine or triethylamine, in which case, as inert solvent, there can be used, for example, diethyl ether, benzene, methylene chloride, dioxane or an excess of the tertiary amine. The amines of general formula (II) can also be used in the form of their acid-addition salts, for example as hydrochlorides.

In the case of the use of inorganic acid binders, as reaction medium there can be used, for example, water, aqueous ethanol or aqueous dioxane.

For the alkylation of the sulphonamides (IV), there are used compounds (V) in which X is a halogen atom, for example chlorine or bromine, but preferably those in which X is an arylsulphonyloxy radical. Thus, as alkylation agents, there are preferably used arylsulphonic acid alkyl esters, a method, the use of which for sulphonic acid amides, is described, for example, by Klamann en al., Monatshefte für Chemie, 83, 871/1952. The reaction takes place in an alkaline medium, a preferred reaction medium being a hot, concentrated solution of sodium carbonate. If, on the other hand, X is a halogen atom, then an alkali metal salt of the sulphonamide (IV), for example the sodium salt, is reacted with (V) (X=chlorine or bromide) in a polar solvent, for example dimethylformamide. In order to avoid a disubstitution of the sulphonamide (IV), is preferably used in excess.

If, subsequent to the sulphonamide formation, an $R^3$ group is to be introduced, then this takes place by reaction of a compound (I), in which $R^3$ is a hydrogen atom, with an acid halide when $R^3$ is an acyl radical. For all other meanings of $R^3$, there is used a halide (chloride or bromide) of general formula (VI), working being under the above-described conditions.

The acylation of the sulphonamide takes place in an inert solvent, for example diethyl ether or methylene chloride, and as acid-bonding agent there is preferably used an organic base, for example pyridine or triethylamine.

The conversions in the A radical possibly subsequent to the sulphonamide formation and possibly after the introduction of an $R^3$ group can be described as follows:

For the conversion of a carbonyl group into a hydroxyl group, there can be used all conventional processes. Preferred is the reduction with complex hydrides, for example with sodium borohydride, protic solvents, for example water, (aqueous) alcohols aqueous dioxane, thereby being used as reaction medium. In the case of the absence of other reducable groups the reduction can also be carried out with complex aluminium hydrides, for example lithium aluminium hydride, in which case aprotic solvents, for example diethyl ether, tetrahydrofuran or dioxane, here serve as reaction medium. However, the carbonyl reduction can take place with catalytically activated hydrogen, for example with hydrogen/Raney nickel, or by reaction with nickel-aluminium alloy in aqueous alkali.

For the reduction of the carboxyl function, there can be used all conventional reducing agents, for example complex hydrides, such as lithium aluminium hydride, or boran adducts, for example $BH_3.THF$. However, the reduction can also take place advantageously by the reduction of a derivative of the carboxylic acid, for example of a mixed anhydride of the carboxylic acid and of a carbonic acid hemiester. As reducing agent, there are here preferably used complex boron hydrides, for example sodium borohydride, in a protic solvent.

Derivatives of the carboxylic acids suitable for the reduction are, for example, also the esters thereof which can be reacted to give primary alcohols by methods known from the literature. Here, too, preferred reducing agents are complex aluminium hydrides, for example lithium aluminium hydride.

If the carboxyl function is to be reduced without an oxo group simultaneously present in A also being reduced, then the latter is to be protected temporarily, for example by ketalisation. Such hydroxyketones can also be prepared by reducing not only the keto group but also the carboxyl function, in which case there are obtained diols which are also within the scope of the present invention, and subsequently the secondary hydroxyl function is selectively oxidised to the keto function. For this purpose, there can be used, for example, active manganese dioxide.

The etherification of cycloalkanols of general formula (VII) with halocarboxylic acids takes place in the presence of alcoholate-forming agents, for example sodium hydride, but preferably n-butyl lithium under phase transfer conditions, i.e. in a mixture of an aqueous solution of an alkali, a suitable organic solvent, for example methylene chloride, and in the presence of a quaternary ammonium salt, for example tetra-n-butylammonium bromide. The subsequent splitting off of protective-groups Z and $R^3$ of general formula (VII) can, of course, be omitted when Z is already a group of the general formula:

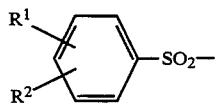

and $R^3$ has the above-mentioned meaning other than being a hydrogen atom.

For the preparation of compounds (I) in which A is a 1H-tetrazol-5-yl radical, nitriles are used as starting materials which are cyclised with hydrazoic acid or preferably with a salt thereof to give the tetrazol group:

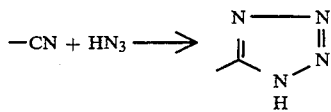

The salts of hydrazoic acid which, in the process according to the present invention, are reacted with nitriles, can be, for example, alkali metal salts, for example lithium azide, sodium azide and potassium azide, alkaline earth metal salts, for example magnesium azide, calcium azide or strontium azide, or metal salts, for example aluminium azide, tin azide, zinc azide or titanium azide, ammonium azide or salts with organic bases, for example aniline azide and the like. In some cases, it is expedient not to use the pure azides but rather to react them in mixtures with, for example, ammonium chloride or an alkylammonium chloride or also in combination with a Lewis acid, for example aluminium chloride, tin chloride, zinc chloride or titanium tetrachloride.

The hydrazoic acid or salts thereof, as well as the Lewis acid or ammonium chloride or alkylammonium chloride which are used in combination with the alkali metal azides are used in 1 to 10 molar excess, referred to the nitriles.

For the preparation of salts of pharmacologically acceptable organic or inorganic bases, for example sodium hydroxide, potassium hydroxide, calcium hydroxide, ammonium hydroxide, methylglucamine, morpholine or ethanolamine, the carboxylic acids can be reacted with the appropriate bases. Mixtures of the carboxylic acids with an appropriate alkali metal carbonate or hydrogen carbonate can also be used.

The amines of general formula (II), in which B is a cyclohexylidene radical, required as starting materials for the preparation of compounds of general formula (I) are advantageously prepared by the hydrogenation of the aromatic analogues of the general formula:

(IX)

The compounds of general formula (IV) and (VII) and the precursors thereof are known from European Patent Specifications Nos. 0,031,954, 0,221,344 and 0,239,907. The hydrogenation takes place in the presence of metal catalysts, for example platinum, ruthenium or rhodium, possibly in the form of their oxides, for example ruthenium dioxide, at an elevated pressure, for example of from 50 to 150 bar, and at an elevated temperature, for example of from 70° to 100° C. As solvents, there are preferably used lower aliphatic carboxylic acids, for example acetic acid, or of particular alcohols, for example ethanol.

If in general formula (IX), A is a $-CO-R^4$ radical, then, for the preparation of the amines (II), the carbonyl compound is first reduced to the carbinol and the aromatic nucleus is then subsequently hydrogenated under gentle conditions, for example at about 50° C., in the presence of platinum dioxide or ruthenium dioxide in ethanol. The carbinol group is thereafter again oxidised to the oxo group.

For the preparation of compounds (II) in which A has, for example, the meaning —COCH₂CH₂COOH, there can be used the reaction according to the following scheme:

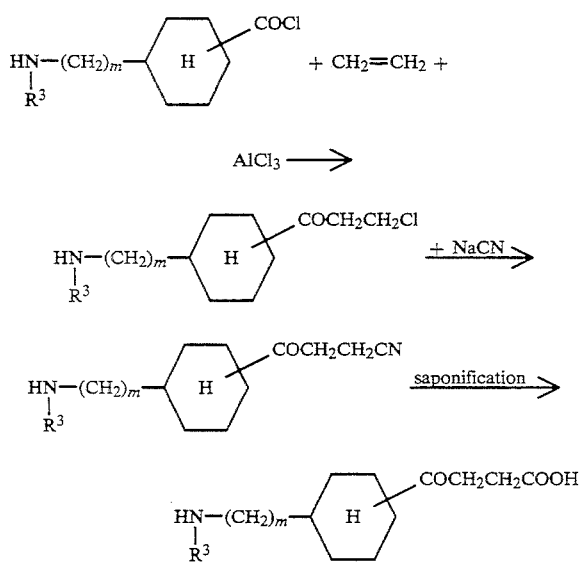

For the preparation of pharmaceutical compositions, the compounds of general formula (I) are mixed in known manner with appropriate pharmaceutical carrier materials, aroma, flavouring and colouring materials and formed, for example, into tablets or dragees or, with the addition of appropriate adjuvants, suspended or dissolved in water or in an oil, for example olive oil.

The compounds of general formula (I) can be administered orally or parenterally in liquid or solid form. As injection medium, it is preferred to use water which contains the stabilising agents, solubilising agents and/or buffers usual in the case of injection solutions. Additives of this type include, for example tartrate and borate buffers, ethanol, dimethyl sulphoxide, complex formers (such as ethylenediaminetetraacetic acid), high molecular weight polymers (such as liquid polyethylene oxide) for viscosity regulation and polyethylene derivatives of sorbitan anhydrides.

Solid carrier materials can be, for example, starch, lactose, mannitol, methylcellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions which are suitable for oral administration can, if desired, contain flavouring and sweetening materials.

The dosage administered depends upon the age, state of health and weight of the recipient, the extent of the disease, the nature of further treatments possibly carried out simultaneously, the frequency of the treatments and the nature of the desired action. Usually, the daily dose of the active compounds is from 0.1 to 50 mg./kg. of body weight. Normally, 0.5 to 40 and preferably 1.0 to 20 mg./kg./day in one or more administrations per day are effective in order to obtain the desired results.

Apart from the compounds described in the Examples, preferred compounds according to the present invention also include the following:
1. 3- [2- (4-chlorobenzenesulphonylamino) -ethyl]-cyclohexyloxyacetic acid; mp. 105°14 106° C.
2. 3-[2-(4-chlorobenzenesulphonylamino)-ethyl]-cyclohexyloxyacetic acid (tetrazol-5-yl-amide); mp. 185°–188° C.
3. cis-4-[2-(4-chlorobenzenesulphonylamino)-ethyl]-cyclohexylacetic acid
4. trans-4-[2-(4-chlorobenzenesulphonylamino)-ethyl]-cyclohexylacetic acid
5. 4-{4-[2-(4-chlorobenzenesulphonylamino)-ethyl]- cyclohexyl}-4-oxobutanoic acid
6. 4-{4-[2-(4-chlorobenzenesulphonylamino) -ethyl]-cyclohexyl}-4-hydroxybutanoic acid
7. 1-{4-[2-(4-chlorobenzenesulphonylamino)-ethyl]-cyclohexyl}-1,4-butanediol
8. 1-butanoyl-4-[2-(4-chlorobenzenesulphonylamino)-ethyl ]-cyclohexane
9. 1-{4-[2-(4-chlorobenzenesulphonylamino)-ethyl]-cyclohexyl}-1-hydroxybutane
10. 1-{4-[2-(4-chlorobenzenesulphonylamino)-ethyl]-cyclohexyl}-butane
11. 1-[2-(4-chlorobenzenesulphonylamino)-ethyl]-3-(1H-tetrazol-5-yl-methyleneoxy)-cyclohexane
12. 1-[2-(4-chlorobenzenesulphonylamino)-ethyl]-4-(1H-tetrazol-5-yl-methyl)-cyclohexane
13. N-(4-chlorobenzenesulphonyl)-0-[4-(2-hydroxyethyl)-cyclohexylmethyl]-hydroxylamine
14. -[2-(4-chlorobenzenesulphonylamino)-ethyl]-[4-(carboxymethyl)-cyclohexyl]ether
15. 4-[2-(4-chlorobenzenesulphonylamino)-1-oxoethyl]-cyclohexane-carboxylic acid
16. 4-[2-(4-chlorobenzenesulphonylamino)-1-hydroxyethyl-cyclohexane-carboxylic acid
17. 4-[2-(4-chlorobenzenesulphonylamino)-ethyl]-cyclohexyloxyacetic acid hydroxylamide
18. 4-[2-(4-chlorobenzenesulphonylamino)-ethyl]-cyclohexylacetic amide; mp. 140°–141° C.

The following Examples are given for the purpose of illustrating the present invention:

EXAMPLE 1

4-[2-(Benzenesulphonylamino)-ethyl]-cyclohexyloxyacetic acid.

a) Ethyl 4-(2-acetaminoethyl)-cyclohexyloxyacetate.

A mixture of 20.0 g. (75 mMol) ethyl 4-[2-acetaminoethyl]-phenoxyacetate, 250 ml. ethanol and 0.7 g. ruthenium dioxide is hydrogenated for 12 hours at 70° C. and 60 bar pressure, filtered and the filtrate quantitative yield of colourless oil.

b) Ethyl 4-(2-aminoethyl)-cyclohexyloxyacetate.

A mixture of 17.0 g. (70 mMol) of the ethyl ester obtained according to a) and 100 mi. 2N hydrochloric acid is kept at reflux temperature for 8 hours. The reaction mixture is then evaporated, 50 ml. ethanol are added to the residue and a spatula tip of p-toluenesulphonic acid and the reaction mixture then maintained for 6 hours at reflux temperature, whereafter the reaction mixture is evaporated. Yield 17.0 g. (91% of theory) of colourless oil.

¹H-NMR (300 MHz, d₆-DMSO): δ=1.2(t, J=7 Hz, 3H, OCH₂CH₃); 3.97 (s, 2H, OCH₂); 4.10 (q, 7 Hz, 2H, OCH₂CH₃).

c) Ethyl 4-[2-(benzenesulphonylamino)-ethyl]-cyclohexyloxyacetate.

To an ice-cold solution of 8.5 g. (30 mMole) ethyl 4-(2-aminoethyl)-cyclohexyloxyacetate and 75 mi. pyridine is added dropwise, while stirring, 5.5 g. (30 mMol) benzenesulphonyl chloride and then left to react for 1 hour at ambient temperature and for 1 hour at 60° C., cooled and poured into an ice-sale mixture. This is extracted with methylene chloride and the methylene chloride phase is washed twice with dilute hydrochloric acid and twice with water, dried over anhydrous magnesium sulphate and evaporated. Yield 10.6 g. (89% of theory) of colourless oil.

d) Title compound.

A mixture of 7.4 g. (20 mMol) of the ethyl ester obtained according to c), 85 ml. 1N aqueous sodium hydroxide solution and 85 mi. methanol is kept at reflux temperature for 8 hours. The methanol is then distilled off and the aqueous phase is extracted twice with diethyl ether. It is then acidified and extracted with methylene chloride. The methylene chloride phase is dried with anhydrous magnesium sulphate and evaporated. The free acid (5.0 g., yield 69% of theory) is then mixed with the calculated amount of sodium hydrogen carbonate in aqueous solution and evaporated. Digestion with a mixture of 1 volume of diethyl ether and 1 volume of ethanol gives the crystalline sodium salt. Yield 72% of theory; m.p. 135°–136° C.

Example 2.

4-2-(4-Chlorobenzenesulphonylamino)-ethyl]-cyclohexanecarboxylic acid.

a) Ethyl 4-(2-aminoethyl)-cyclohexanecarboxylate.

A mixture of 15.0 g. (65 mMol) ethyl 4-(2-aminoethyl)-benzoate hydrochloride 300 ml ethanol and 1 g. ruthenium dioxide is hydrogenated for 10 hours at 100 bar pressure and 90° C., the catalyst is filtered off with suction and the filtrate is evaporated. The crude product is dissolved is hot ethyl acetate, then cooled in an icebath and the compound precipitated out by the addition of isohexane. Yield 11.4 g. (74% of theory) of hydrochloride; m.p. 114°–116° C.

b) Ethyl 4- [2- (4-chlorobenzenesulphonylamino)-ethyl]-cyclohexanecarboxylate.

A mixture of 5.5 g. (23.3 mMole) ethyl 4- (2aminoethyl) -cyclohexanecarboxylate, 50 ml. methylene chloride and 5.9 g. (58 mMole) triethylamine is stirred for 30 minutes at ambient temperature, cooled in an icebath and a solution of 4.92 g. (23.3 mMol) 4-chlorobenzenesulphonyl chloride and 50 mi. methylene chloride added dropwise thereto in the course of 20 minutes. Stirring is then continued for 1 hour at 20° C., then extracted twice with cold 2N hydrochloric acid and twice with water and the methylene chloride phase is dried with anhydrous sodium sulphate. There are obtained 8.59 g. (98% of theory) of product in the form of a colourless oil.

1H-NMR (300 MHz, $d_6$-DMSO): $\delta$=2.72 - 2.82 (m, 2H, NHCH$_2$)

c) Title compound.

A mixture of 7.94 g. (21 mMol) of the compound obtained according to b) 25 ml 2N aqueous sodium hydroxide solution and 20 mi. ethanol is kept for 3 hours at 50°–60° C. and the ethanol then distilled off in a vacuum. After the addition or 0.5N aqueous sodium hydroxide solution, it is extracted with diethyl ether and the aqueous phase is acidified with 2N hydrochloric acid. The oily acid which separates out is taken up in diethyl ether, dried with anhydrous sodium sulphate and evaporated. Yield 6.52 g. (89% of theory); m.p. 127°–128° C., after recrystallisation from ethanol.

The following compounds are obtained in an analogous way:

EXAMPLE 2.2

4-[2-(4-Chlorobenzenesulphonamino)-ethyl],cyclohexyl-acetic acid via the following steps:

a) ethyl 4-(2-aminoethyl)-Cyclohexyl-acetate by hydrogenation of ethyl 4-(aminoethyl)-phenylacetate hydrochloride in the presence of ruthenium dioxide in ethanol. Yield 90% of theory; hydrochloride m.p. 108°–110° C.

b) ethyl 4-[2-(4-chlorobenzenesulphonylamino)-ethyl]-cyclohexylacetate by reaction of the product obtained according to a) with 4-chlorobenzenesulpochloride in pyridine. Yield 91% of theory; m.p. 63 - 65° C.

c) Title compound by saponification of the ethyl ester with 2N sodium hydroxide solution in ethanol. Yield 84% of theory; acid m.p. 110°–111° C., after recrystallisation from ethanol/water (2:1 v/v).

EXAMPLE 2.3

3-[4-(2-Benzenesulphonylaminoethyl)-cyclohexyl]-propionic acid via the following steps:

a) methyl 3-[4-(2-acetaminoethyl)-cyclohexyl]-propionate by the hydrogenation of methyl 3-[4-(2-acetaminoethyl)-phenyl ]-propionate in the presence of ruthenium dioxide in ethanol. Yield 82% of theory, semi-crystalline product.

1H-NMR (300 MHz, $d_6$-DMSO): $\delta$=1.76 (s, 3H, CH$_3$CO); 2.28 (6, J=7 Hz, 2H, CH$_2$COOMe); 3.57 (s, 3H, OCH$_3$).

b) 3-[4-(2-aminoethyl)-cyclohexyl]propionic acid by hydrolysis with 6N hydrochloric acid.

Yield 75% of theory; hydrochloride m.p. 215°–216° C.

c) ethyl 3-[4-(2-aminoethyl)-cyclohexyl]-propionate by gassing an ethanolic solution of the acid with hydrogen chloride. Yield 81% of theory; hydrochloride semi-crystalline mass.

d) ethyl 3-4-[2-(benzenesulphonylamino)-ethyl]-cyclohexyl propionate by reacting the product obtained according to c) with benzenesulpochloride in pyridine. Yield 76% of theory; colourless oil.

1H-NMR (300 MHz, $d_6$-DMSO): $\delta$=2.20–2.28 (m, 2H, CH$_2$COOC$_2$H5); 2.70–2.80 (m, 2H, NHCH$_2$); 7.45 (t, J=4 Hz, 1H, NHSO$_2$); 7.53–7.81 (m, 4H, aromatic protons)

e) Title compound by saponification of the ethyl ester with 2N sodium hydroxide solution in methanol and neutralisation of the free acid with sodium hydrogen carbonate. Yield 68% of theory; sodium salt m.p. 297°–301° C.

EXAMPLE 2.4

4-[3-(4-Chlorobenzenesulphonylamino)-propyl]-cyclohexylacetic acid via the following steps:

a) ethyl 4-(3-aminopropyl)-cyclohexyl-acetate by hydrogenation of ethyl 4-(3-aminopropyl)-phenylacetate hydrochloride in the presence of rhodium in ethanol. Yield 90% of theory; m.p. 99°–103° C.

b) ethyl 4-[3-(4-chlorobenzenesulphonylamino)-propyl]-cyclohexylacetate by reaction of the product obtained according to a) with 4-chlorobenzenesulphochloride in the presence of triethylamine in methylene chloride. Yield 95of theory, colourless oil.

IR 48438, NMR V 3731

$^1$H-NMR (300 MHz, d$_6$-DMSO): δ=1.17 (t, 3H, OCH$_2$CH$_3$); (2.12 and) 2.22 (d, J=Y Hz, 2H (additional 2H) CH$_2$-COOEt, cis/trans mixture; 4.04 (q, 2H, OCH$_2$CH$_3$); 7.55-7.81 (4H, m, aromatic H).

c) Title compound by saponification of the ethyl ester by means of 2N sodium hydroxide solution in ethanol. Yield 81% of theory; m.p. 139°-141° C., after recrystallisation from 60% ethanol.

EXAMPLE 2.5

5-[4-(2 -(4-Chlorobenzenesulphonylamino)-ethyl)-cyclohexyl]-pentanoic acid via the following steps:

a) ethyl 5-[4-(2-aminoethyl)-cyclohexyl]-pentanoate hydrochloride by hydrogenation of ethyl 5-[4-(2-aminoethyl)-phenyl]-pentanoate hydrochloride in the presence of platinum in glacial acetic acid. Yield 57% of theory; hydrochloride wax-like substance.

b) ethyl 5-[4-(2-(4-chlorobenzenesulphonylamino)-ethyl)-cyclohexyl]-pentanoate by reaction of the product obtained according to a) with 4-chlorobenzenesulphochloride in methylene chloride in the presence of triethylamine. Yield 72% of theory, colourless oil.

$^1$H-NMR (300 MHz, d$_6$-DMSO): δ=1.17 (t, J=7 Hz, 3H, OCH$_2$CH$_3$); 2.24 (t, J=7 Hz, 2H, CH$_2$COOEt); 4.04 (q, J=7 Hz, 2H, OCH$_2$CH$_3$); 7.55 (t, J=5 Hz, 1H, —SO$_2$NH); 7.62-6.82 (m, AH, aromatic protons).

c) Title compound by saponification of the ethyl ester with 2N sodium hydroxide solution in methanol. Yield 85% of theory; m.p. 98°-100° C.

EXAMPLE 2.6

4 -[2-(4-Bromobenzenesulphonylamino)-ethyl]-cyclohexylacetic acid via the following steps:

a) ethyl 4-[2-(4-bromobenzenesulphonylamino)-ethyl]-cyclohexylacetate by the reaction of ethyl 4-(2-aminoethyl)-cyclohexyl acetate hydrochloride with 4-bromobenzenesulphochloride in methylene chloride in the presence of triethylamine. Yield 74% of theory; m.p. 62° C.

b) title compound by saponification of the ethyl ester with 2N sodium hydroxide in ethanol. Yield 85% of theory; m.p. 124°-126° C., after recrystallisation from toluene.

EXAMPLE 2.7

4-[2-(4-Methylbenzenesulphonylamino)-ethyl]-cyclohexylacetic acid via the following steps:

a) ethyl 4-[2-(4-methylbenzenesulphonylamino)-ethyl]-cyclohexylacetate by the reaction of ethyl 4-(2-aminoethyl)-cyclohexy-lacetate hydrochloride with p-toluenesulphochloride in methylene chloride in the presence of triethylamine. Yield 79% of theory; colourless oil; n=1.5202.

$^1$H-NMR (300 MHz, d$_6$-DMSO): δ=2.12 and 2.20 -2d, J=7 Hz, addl. 2H, -CH$_2$COOEt); 2.68-2.78 (m, 2H, NHCH$_2$); 7.30-7.70 (m, 5H, -NHSO$_2$ and aromatic protons).

b) title compound by saponification of the ethyl ester with 2N sodium hydroxide solution in ethanol. Yield 72% of theory; m.p. 104°-105° C., recrystallised from toluene.

EXAMPLE 2.8

Ethyl 4-[2-(4-cyanobenzenesulphonylamino)-ethyl]-cyclohexylacetate by the reaction of 4-cyanobenzenesulphonylchloride with ethyl 4-(2-aminoethyl)-cyclohexylacetate hydrochloride in methylene chloride in the presence of triethylamine. Yield 95% of theory, colourless oil. $^1$H-NMR (300 MHz, d$_6$-DMSO): δ=2.12 and 2.21 (2d, J=7 Hz, addl. 2H, CH$_2$COOEt); 2.75-2.85 (m, 2H, NHCH$_2$); 7.78 (t, J=4 Hz, 1H, SO$_2$NH); 7.91-8.08 (m, 4H, aromatic protons).

EXAMPLE 2.9

4-[2-(4-Aminocarbonylbenzenesulphonylamino)-ethyl]-cyclohexylacetic acid by saponification of the ethyl 4-[2-(4-cyanobenzenesulphonylamino)-ethyl]-cyclohexylacetate with 2N sodium hydroxide solution in ethanol analogously to EXAMPLE 2c). Yield 72% of theory; m.p. 172-174° C. after recrystallisation from isopropanol.

EXAMPLE 3 cis -and trans-4-[2-(4-Chlorobenzenesulphonylamino)-ethyl-cyclohexyloxyacetic acid a) Ethyl cis- and trans 4-[2-(4-chlorobenzenesulphonylamino)-ethyl]-cyclohexyloxyacetate by the reaction of ethyl cis/trans-4-(2-aminoethyl)-cyclohexyloxyacetate with 4-chlorobenzenesulphonyl chloride analogously to EXAMPLE 1c). Yield 95% of theory of a mixture of 80% cis and 20% trans compound; m.p 47°-53° C.

After separation with a preparative average pressure liquid chromatography column (Lichroprep CN/cyclohexane/diethyl ether 1.7:1 v/v), there are obtained:

64% of theory of pure cis isomer; m.p. 65° C. and
9% of theory of pure trans isomer; m.p. 75°-77° C.

cis: $^1$H-NMR (300 MHz, d$_6$-DMSO): δ=1.19 (3H, CH$_3$); 1.1-1.4 (7H); 1.70 (2H, H eq.); 2.78 (2H, N—CH$_2$—); 3.50 (1H, H eq.); 4.02 (2H, CH$_2$); 4.10 (H, OCH$_2$—); 7.56 (1H, NH); 7.65 (2H, H aromatic); 7.78 (2H, H aromatic).

trans: $^1$H-NMR (300 MHz, d$_6$-DMSO): δ=0.82 (2H, H ax.); 1.08 (3H, H ax.); 11.19 (3H, —CH$_3$); 1.25 (2H, CH$_2$); 1.59 (2H, H eq.); 1.93 (2H, H eq.); 2.77 (2H, N—CH$_2$); 3.19 (1H, H ax.); 4.05 (2H, CH$_2$); 4.10 (2H, O—CH$_2$); 7.55 (1H, NH); 7.64 (2H, H aromatic); 7.78 (2H, H aromatic).

b) cis- and trans-4-[2-(4-chlorobenzenesulphonylamino)-ethyl]-cyclohexyloxyacetic acid.

A mixture of 3.0 g. (7.4 mMol) of cis ester, 30 ml. ethanol and 12 ml. 2N sodium hydroxide solution is maintained for 3 hours at 50° C. and the ethanol subsequently distilled off. The residue is diluted with 20 ml. water, then acidified by the dropwise addition of 2N hydrochloric acid, filtered off with suction and dried. Yield 2.6 g. (93% of theory) of cis acid; m.p. 105°-106° C., after recrystallisation from ethyl acetate. $^1$H-NMR (300 MHz, d$_6$-DMSO): δ=1.1-1.4 (7H); 1.70 (2H, H eq.); 2.78 (2H, N—CH$_2$); 3.50 (1H, H eq.); 2.93 (2H, CH$_2$); 7.56 (1H, NH); 7.65 (2H, H aromatic); 7.78 (2H, H aromatic).

In an analogous manner, from the trans ester there is obtained the trans acid; m.p. 118°–120° C. $^1$H-NMR (300 MHz, d$_6$-DMSO): δ0.82 (2H, H ax.); 1.07 (2H, H ax.); 1.18 (1H, ax.); 1.23 (2H, CH$_2$); 1.58 (2H, H eq.); 1.92 (2H, eq.); 2.76 (2H, B—CH$_2$); 3.19 (1H, H ax.); 3.96 (2H, CH$_2$); 7.55 (1H, NH); 7.64 (2H, H aromatic); 7.78 (2H, H aromatic).

EXAMPLE 4 cis-4-[2-(4-Chlorobenzenesulphonylamino)-ethyl]cyclohexyloxyacetic acid (tetrazol-5-yl)-amide.

To a solution of 2.0 g. (5.3 mMol) cis-4-[2-(4-chlorobenzenesulphonylamino)-ethyl]-cyclohexylacetic acid and 25 ml. anhydrous tetrahydrofuran is added dropwise 0.86 g. (5.3 mMol) carbonyl-bisimidazole. The reaction mixture is stirred for 10 minutes,. 0.74 g. (5.3 mMol) 4-nitrophenol is added thereto, followed by further stirring for 10 minutes am 40° C. 0.91 g. (100 mMol) anhydrous 5-amino-1, 2,3,4-tetrazole is then added thereto. The reaction mixture is kept at 60° C. for 3 hours, then evaporated in a vacuum and the residue is stirred with 0.5N hydrochloric acid. After filtering off with suction and washing with water, the product obtained is recrystallised from ethanol. Yield 1.40 g. (59% of theory); m.p. 191°–192° C.

In an analogous manner, there is obtained trans-4-[2-(4-chlorobenzenesulphonylamino)-ethyl]-cyclohexyloxy acetic acid (tetrazol-5-yl-amide); yield 73% of theory; m.p. 214° C., after recrystallisation from ethanol.

EXAMPLE 5

Ethyl trans-4-[2-(N-benzoyl-4-chlorobenzenesulphonyl-amino)-ethyl]-cyclohexyloxyacetate.

To an ice-cold mixture of 4.0 g. (10 mMol) ethyl trans-4-[2-(4-chlorobenzenesulphonylamino)-ethyl]-cyclohexyloxyacetate, 50 ml. methylene chloride and 1.5 g. (15 mMol) triethylamine is added dropwise a mixture of 1.4 g. (10 mMol) benzoyl chloride and 30 ml. methylene chloride. The reaction mixture is maintained for 4 hours at reflux temperature, cooled, filtered and the filtrate washed with dilute hydrochloric acid and water. It is then dried with anhydrous sodium sulphate and evaporated After purification over silica gel/ cyclohexane/diethyl ether (2:1 v/v), there is obtained a yield of 1.7 g (67% of theory); m.p. 81°–82° C.

EXAMPLE 6.

4-[2-(4-Chlorobenzenesulphonylamino)-ethyl]-cyclohexylacetic acid (tetrazol-5-yl-amide).

This is obtained analogously to Example 4 from 4-[2-(4-chlorobenzenesulphonylamino)-ethyl]-cyclohexylacetic acid and 5-amino1,2,3,4-tetrazole; m.p. 216° C. (decomp.) after recrystallisation from ethanol.

EXAMPLE 7.

1-[2-(4-Chlorobenzenesulphonylamino)-ethyl]-4-(tetrazol-5-yl -methyleneoxy)-cyclohexane.

a)4-[2-(4-Chlorobenzenesulphonylamino)-ethyl]cyclohexyloxyacetamide.

To a mixture of 4.5 g. (12 mMol) 4-[2-(4-chlorobenzenesulphonylamino)-ethyl]-cyclohexyloxyacetic acid, 25 ml. anhydrous tetrahydrofuran and 1.43 g. (14 mMol) triethylamine is slowly added dropwise at −15° C. a solution of 1.33 g. (12 mMol) ethyl chloroformate and 10 ml. anhydrous tetrahydrofuran, whereafter the reaction mixture is allowed to warm up to 20° C. it is then filtered off with suction and ammonia passed into the filtrate at ambient temperature. The reaction mixture is stirred for a further 2 hours, filtered and the filtrate evaporated and brought to crystallisation by the addition of isohexane. Yield 4.3 g. (96% of theory); m.p. 105°–108° C.

b) 4-[2 (4-Chlorobenzenesulphonylamino)-ethyl]-cyclohexyloxyacetonitrile.

A mixture of 4.0 g. (10 mMol) of the carbonamide obtained according to a), 50 ml. toluene and 3.0 g. (20 mMol) phosphorus pentoxide is kept at 110° C. for 3 hours and then cooled. After the addition of water, it is extracted with ethyl acetate and the organic phase is dried with anhydrous sodium sulphate and evaporated. Yield 2.8 g. (74% of theory), colourless oil.

$^1$H-NMR (300 MHz, d$_6$-DMSO): δ=2.73–2.83 (m, 2H, NHCH$_2$); 4.39 (s, 2H, OCH$_2$CN); 7.55 (t, J=6 Hz, 1H, NHSO$_2$); 7.63–7.83 (m, 4H, aromatic protons).

c) title compound.

A mixture of 2.5 g. (7 mMol) of the nitrile obtained according to b), 70 ml. 1-methylpyrrolidone, 1.49 g. (10 mMol) triethylammonium chloride and 1.40 g. (20 mMol) sodium azide is stirred for 6 hours at 150° C. The 1-methylpyrrolidone is then distilled off in a vacuum and the residue is dissolved in a dilute aqueous solution of sodium hydroxide and extracted three times with diethyl ether. The aqueous solution is acidified with 6N hydrochloric acid and then extracted four times with ethyl acetate. The extract is dried with anhydrous sodium sulphate and evaporated. Yield 2.1 g. (75% of theory); m.p. 122°–123° C.

EXAMPLE 7

Blood Platelet Aggregation Inhibitor Effects (a) In vitro Inhibition of Platelet Aggregation.

Platelet-rich human blood plasma was treated with 3.2% citrate at a volume ratio of 1:9 to inhibit clotting. A selective thromboxane mimetic, U46619, which is a stable analog of the prostaglandin endoperoxide PGH$_2$, as described by Coleman et al., Brit. J. Pharmocol. 68,127P (1980) was obtained from Upjohn & Co., Kalamazoo, Mich.

The test protocol was that described by Born and Cross, J. Physiol. 168,178 (1963) with the degree of aggregation measured using a 4-channel aggregometer (Profiler, Bio/Data Co.). The compounds of this invention, Examples 2.1, 4(cis) 4(trans), 6 ad 7 were diluted in saline, at final concentrations of 10−4 to 10−9M. Saline was used as a control. Measurements were made for a period of five minutes, After addition of the tromboxane mimetic. From the data obtained, an inhibitory concentration IC$_{50}$ was calculated using standard methods. The results are shown in Table 1.

(b) In vivo Inhibition of Induced Pulmonary Emboli

Male NMRI mice, having a body weight of approximately 25g, were separated into groups of 5. Representative examples of the compounds of this invention listed in part (a) were suspended 1% methyl cellulose and administered to the animals by gastric incubation in amounts providing 1/mg/kg and 25/mg/kg of the antagonist, Four hours after incubation, a previously determined lethal dose of U46619 (800–1000 ug/kg) was injected into the tail vein of each animals. The survival rates for each group of mice was determined after 24 hours. The results are shown in Table 1 and indicate correlation with the IC$_{50}$ measured in vitro.

TABLE 1

| Example | Survival Rate of Mouse 25 mg/kg, 4 h in % | Survival Rate of Mouse 1 mg/kg, 4 h in % | Thromboxane Aggregation IC$_{50}$ (μM) |
|---|---|---|---|
| 2.1 | 100 | 100 | 2.0 |
| 4 (cis) | 100 | 100 | 4.6 |
| 4 (trans) | 100 | 60 | 5.8 |
| 6 | 100 | 100 | 2.5 |
| 7 | 100 | 100 | 0.42 |

We claim:

1. Sulphonamides having the structural formula (I):

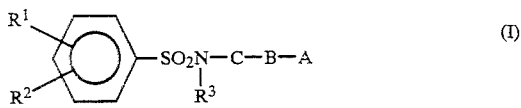

wherein R and R$^2$ which may be the same or different are selected from the group consisting of hydrogen, halogen, C$_1$-C$_6$-alkyl, trifluoromethyl, cyano, carboxyl, alkoxycarbonyl, aminocarbonyl, N-alkylaminocarbonyl and N, N-dialkylaminocarbonyl, and when R$^1$ and R$^2$ are alkyl and ortho to one another, R$^1$ and R$^2$, together with the carbon atoms to which they are attached, form a saturated or unsaturated C$_5$-C$_7$-alkylene ring, R$^3$ is selected from the group consisting of hydrogen, C$_1$-C$_6$-alkyl, formyl, C$_1$-C$_6$-alkylcarbonyl, phenyl—C$_1$-C$_6$-alkyl, benzoyl and phenyl-C$_2$-C$_6$-alkenyl, the phenyl moieties being optionally substituted with halogen, alkyl or trifluoromethyl, C is selected from the group consisting of —(CH$_2$)$_m$— wherein m is 2 or 3, or branched C$_2$-C$_5$-alkylene, wherein the methylene radical —CH$_2$— of the group C may be replaced by oxygen, sulphur, a hydroxymethylene radical —CHOH— or carbonyl group —CO—, B is a 1,2-, 1,3-, 1,4-cyclohexylidene or 1,2-or 1,3-cyclopentylidene, and A is selected from the group consisting of carboxyl, carboxy-C$_1$-C$_6$-alkyl, carboxy-C$_1$-C$_6$-alkoxy, a —D—R$^4$ radical, in which D is —CO— and R$^4$ is carboxyl, or carboxy-C$_1$-C$_5$-alkyl, as well as pharmacologically acceptable salts, and amides thereof, all optically-active forms and all the cis and trans isomers thereof.

2. Sulphonamides according to claim 1, wherein at least one of R$^1$ and R$^2$ is selected from the groups consisting of hydrogen, halogen, C$_1$-C$_6$-alkyl, trifluoromethyl, cyano and aminocarbonyl.

3. Sulphonamides according to claim 1, wherein at least one of R$^1$ and R$^2$ is selected from the group consisting of hydrogen, halogen and C$_1$-C$_6$-alkyl.

4. Sulphonamides according to claim 1, wherein R$^3$ is selected from the group consisting of hydrogen, C$_1$-C$_6$-alkyl C$_1$-C$_6$-alkyl-carbonyl, benzoyl, benzyl, phenethyl and cinnamyl.

5. Sulphonamides according to claim 1, wherein R$^3$ is hydrogen or benzoyl.

6. Sulphonamides according to claim 1, wherein C is selected from the group consisting of —(CH$_2$)$_m$—, wherein m is 2 or 3, —O—CH$_2$—, —CH$_2$—CH$_2$—O—, —CH$_2$—CO—and —CH$_2$—CHOH—.

7. Sulphonamides according to claim 1, wherein C is —(CH$_2$)$_2$— or —(CH$_2$)$_3$—.

8. Sulphonamides according to claim 1, wherein B is 1,3-or 1,4-cyclohexylidene.

9. Sulphonamides according to claim 1, wherein A is selected from the group consisting of, carboxyl, carboxy-C$_1$-C$_4$-alkyl, carboxy-C$_1$-C$_4$-alkoxy, and —D—R$^4$ wherein D is a —CO— and R$^4$ is a carboxy-C$^1$-C$^3$-alkyl radical.

10. Sulphonamides according to claim 1, wherein A is carboxy-C$_1$-C$_6$-alkyl or carboxy-C$_1$-C$_6$-alkoxy.

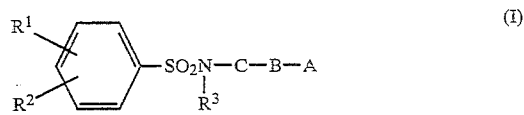

11. Sulphonamides according to claim 1 wherein R$_1$ is halogen and R$_2$ is hydrogen, halogen, trifluoromethyl, cyano and aminocarbonyl.

12. Sulphonamides according to claim 11, wherein R$_1$is chloro or bromo.

13. Sulphonamides according to claim 11, wherein R$_1$ is halogen and R$_2$ is hydrogen.

14. Sulphonamides according to claim 1, wherein A is selected from the group consisting of carboxy-C$_1$-C$_6$-alkyl and carboxy-C$_1$-C$_6$-alkoxy.

15. Sulphonamides according to claim 14, wherein R$_1$ is halogen and R$_2$ is hydrogen, halogen, trifluoromethyl, cyano and aminocarbonyl.

16. A sulphonamide according to claim 16 which is selected from the group consisting of 4-[2-(Benzenesulphonylamino)ethyl]-cyclohexyloxyacetic acid, 4-[2-(4-Chloro benzenesulphonylamino)-ethyl]cyclohexanecarboxylic acid, 4-[2-(4-chlorobenzenesulphonamino)-ethyl]-cyclohexylacetic acid, 4-[2-(4-Bromobenzenesulphonylamino)-ethyl]-cyclohexylacetic acid, 4-[2-(4-Chlorobenzenesulphonylamino)-ethyl]-cyclohexyloxyacetic acid, 4-[2(4-Chlorobenzenesulphonylamino)-ethyl]-cyclohexyloxyacetic acid, and, 4-[2-(N-benzoyl-4-chlorobenzenesulphonylamino)-ethyl]-cyclohexyloxyacetate.

17. A pharmaceutical composition containing at least one sulphonamide according to claim 1 and a pharmaceutically acceptable carrier.

18. A method of inhibiting blood platelet aggregation in a mammal requiring such treatment comprising administering an effective amount of a pharmaceutical composition according to claim 16.

19. A method of preventing or controlling smooth muscle contraction in a mammal requiring such treatment comprising administering an effective amount of a pharmaceutical composition according to claim 1.

20. A method of inhibiting bronchoconstriction in a mammal requiring such treatment comprising administering a bronchoconstriction inhibiting effective amount of a sulphonamide according to claim 1.

21. A method for the prophylactic treatment of mammals at high risk to thromboses comprising administering a platelet-aggregation inhibiting amount of a sulphonamide according to claim 1.

22. A method of preventing or controlling smooth muscle contraction in a mammal requiring such treatment comprising administering an effective amount of a pharmaceutical composition comprising a sulphonamide having the structural (I):

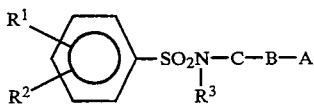

wherein $R^1$ and $R^2$ which may be the same or different, are selected from the group consisting of hydrogen, halogen, $C_1$–$C_6$-alkyl, trifluoromethyl, cyano, carboxyl, alkoxycarbonyl, aminocarbonyl, N-alkylaminocarbonyl and N, N-dialkylaminocarbonyl, and when $R^1$ and $R^2$ are alkyl and ortho to one another, $R^1$ and $R^2$, together with the carbon atoms to which they are attached, form a saturated or unsaturated $C_5$–$C_7$-alkylene ring, $R^3$ is selected from the group consisting of hydrogen, $C_1$–$C_6$-alkyl, formyl, $C_1$–$C_6$-alkylcarbonyl, phenyl-$C_1$–$C_6$-alkyl, benzoyl and phenyl-$C_2$–$C_6$-alkenyl, the phenyl moieties being optionally substituted with halogen, alkyl or trifluoromethyl, C is selected from the group consisting of —$(CH_2)_m$— wherein m is 0, 1, 2 or 3, or branched $C_2$–$C_5$-alkylene, wherein the methylene radical —$CH_2$— of the group C may be replaced by oxygen, sulphur, a hydroxymethylene radical —CHOH— or carbonyl group —CO—, B is a 1,2-, 1,3-, 1,4-cyclohexylidene or 1,2-or 1,3-cyclopentylidene and A is selected from the group consisting of tetrazolyl, tetrazolyl-$C_1$–$C_6$-alkyl, tetrazolyl-$C_1$–$C_6$-alkoxy, tetrazolylaminocarbonyl-$C_1$–$C_6$-alkyl, tetrazolylaminocarbonyl-$C_1$–$C_6$-alkoxy, a —D—$R^4$ radical, in which D is —CO— or —CHOH— and $R^4$ is tetrazolyl or tetrazolyl-$C_1$–$C_5$-alkyl, as well as pharmacologically acceptable salts, and amides thereof, all optically-active forms and all the cis and trans isomers thereof, and a pharmaceutically acceptable carrier.

23. A method of inhibiting bronchoconstriction in a mammal requiring such treatment comprising administering a bronchoconstriction inhibiting effective amount of pharmaceutical composition comprising a sulphonamide having the structural formula (I):

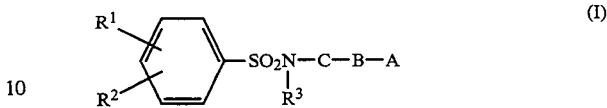

wherein $R^1$ and $R^2$ which may be the same or different are selected from the group consisting of hydrogen, halogen, $C_1$–$C_6$-alkyl, trifluoromethyl, cyano, carboxyl, alkoxycarbonyl, aminocarbonyl, N-alkylaminocarbonyl and N, N-dialkylaminocarbonyl, and when $R^1$ and $R^2$ are alkyl and ortho to one another, $R^1$ and $R^2$ together with the carbon atoms to which they are attached, form a saturated or unsaturated $C_5$–$C_7$-alkyl, benzoyl and phenyl-$C_2$–$C_6$-alkenyl, the phenyl moieties being optionally substituted with halogen, alkyl or trifluoromethyl, C is selected from the group consisting of —$(CH_2)_m$—wherein m is 0, 1, 2 or 3, or branched $C_2$–$C_5$-alkylene, wherein the methylene radical —$CH_2$—of the group C may be replaced by oxygen, sulphur, a hydroxymethylene radical —CHOH— or carbonyl group —CO—, B is a 1,2-, 1,3-, 1,4-cyclohexylidene or 1,2-or 1,3-cyclopentylidene and A is selected from the group consisting of tetrazolyl, tetrazolyl-$C_1$–$C_6$-alkyl, tetrazolylaminocarbonyl-$C_1$–$C_6$alkoxy, a —D—$R^4$ radical, in which D is —CO— or —CHOH— and $R^4$ is tetrazolyl or tetrazolyl-$C_1$–$C_5$-alkyl, as well as pharmacologically acceptable salts, and amides thereof, all optically-active forms and all the cis and trans isomers thereof, and a pharmaceutically acceptable carrier.

* * * * *